(12) United States Patent
Bandi et al.

(10) Patent No.: US 11,471,447 B2
(45) Date of Patent: Oct. 18, 2022

(54) STABLE PHARMACEUTICAL PRODUCT AND VESSEL COMPRISING SODIUM PICOSULFATE, MAGNESIUM OXIDE AND CITRIC ACID

(71) Applicant: Hetero Labs Limited, Hyderabad (IN)

(72) Inventors: Parthasaradhi Reddy Bandi, Hyderabad (IN); Khadgapathi Podile, Hyderabad (IN); Sunil Deviprasad Tiwari, Hyderabad (IN); Vijay Nasare, Hyderabad (IN); Prakash Shetiya, Hyderabad (IN); Patchigolla Satyanarayana Rao, Hyderabad (IN); Chidara Ravi Chandra Gupta, Hyderabad (IN)

(73) Assignee: HETERO LABS LIMITED, Hyderabad (IN)

( * ) Notice: Subject to any disclaimer, the term of this patent is extended or adjusted under 35 U.S.C. 154(b) by 151 days.

(21) Appl. No.: 16/896,744

(22) Filed: Jun. 9, 2020

(65) Prior Publication Data

US 2020/0397767 A1    Dec. 24, 2020

(30) Foreign Application Priority Data

Jun. 20, 2019   (IN) .............................. 201941024546

(51) Int. Cl.
*A61K 31/4402* (2006.01)
*A61K 47/02* (2006.01)
*A61M 3/02* (2006.01)
*A61K 47/12* (2006.01)
*A61K 9/00* (2006.01)

(52) U.S. Cl.
CPC .......... *A61K 31/4402* (2013.01); *A61K 47/02* (2013.01); *A61K 47/12* (2013.01); *A61M 3/02* (2013.01); *A61K 9/0053* (2013.01)

(58) Field of Classification Search
CPC .............. A61K 2300/00; A61K 31/194; A61K 31/4402; A61K 33/08; A61K 47/02; A61K 47/12; A61K 9/0053; A61K 9/0095; A61J 1/05; A61J 1/2093; A61M 3/02; A61P 1/10
See application file for complete search history.

(56) References Cited

U.S. PATENT DOCUMENTS

| | | |
|---|---|---|
| 8,481,083 B2 | 7/2013 | Xu et al. |
| 9,827,231 B2 | 11/2017 | Nam |
| 2011/0076339 A1* | 3/2011 | Vanner ...................... A61P 1/10 424/605 |

* cited by examiner

*Primary Examiner* — Savitha M Rao
(74) *Attorney, Agent, or Firm* — Cantor Colburn LLP

(57) ABSTRACT

Described herein is a stable oral liquid pharmaceutical product comprising sodium picosulfate, magnesium oxide and citric acid. Particularly, sodium picosulfate is physically separated from magnesium oxide and citric acid prior to dispensing and is mixed at the time of administration.

7 Claims, 3 Drawing Sheets

STABLE PHARMACEUTICAL PRODUCT AND VESSEL COMPRISING SODIUM PICOSULFATE, MAGNESIUM OXIDE AND CITRIC ACID

CROSS-REFERENCE TO RELATED APPLICATIONS

This application claims priority to Indian Application IN201941024546 filed on Jun. 20, 2019, which is incorporated herein by reference in its entirety.

FIELD OF THE DISCLOSURE

The present invention provides a liquid pharmaceutical product comprising sodium picosulfate, magnesium oxide and citric acid and process for preparation thereof.

BACKGROUND OF THE DISCLOSURE

A pharmaceutical product used for cleansing of the colon as a preparation for colonoscopy is presently sold under the trade name of PREPOPIK® and CLENPIQ® in the United States as a powder for oral solution and as a ready to use solution respectively. Both PREPOPIK® and CLENPIQ® contain sodium picosulfate, magnesium oxide and citric acid.

U.S. Pat. No. 8,481,083 relates to a process of making a powder for an oral solution comprising the steps of preparing: (a) a core of citric acid, coated with a layer of magnesium oxide; and (b) another core of potassium bicarbonate, spray coated with a layer of sodium picosulfate.

U.S. Pat. No. 9,827,231 relates to a pharmaceutical liquid composition comprising sodium picosulfate, magnesium oxide, citric acid, and malic acid.

As per U.S. Pat. No. 9,827,231, citric acid and magnesium oxide are chief ingredients that may react with each other to provide magnesium citrate, and the unreacted magnesium oxide may accelerate the precipitation of magnesium citrate over time. If the precipitated medicine is taken, a proper effect for colonoscopy preparation cannot be achieved. If the pH of the preparation is kept low, the amount of precipitation tends to be reduced. However, in this case of low pH, there arises a problem that the sodium picosulfate becomes unstable. Therefore, it is difficult to manage precipitation and stability problems.

Accordingly, there is a need for developing liquid pharmaceutical products comprising sodium picosulfate, magnesium oxide and citric acid with improved stability. Therefore, described herein are liquid pharmaceutical products comprising sodium picosulfate, magnesium oxide and citric acid with improved physical and chemical stability.

SUMMARY

In an aspect, described herein is a liquid pharmaceutical product comprising sodium picosulfate, magnesium oxide and citric acid and a process for its preparation.

Another aspect relates to a stable oral liquid pharmaceutical product comprising liquid sodium picosulfate, magnesium oxide and citric acid, wherein the liquid sodium picosulfate is physically separated from the liquid magnesium oxide and the liquid citric acid.

Another aspect relates to a vessel, the vessel comprising sodium picosulfate in a first compartment and a combination of magnesium oxide and citric acid in a second compartment, wherein the first and second compartments are physically separated from one another prior to dispensing, and wherein the vessel permits the components of the first and second compartments to be dispensed together.

In yet another aspect, described herein is a pharmaceutical product and vessel as described above useful for cleansing of the colon as a preparation for colonoscopy.

Figure 1:
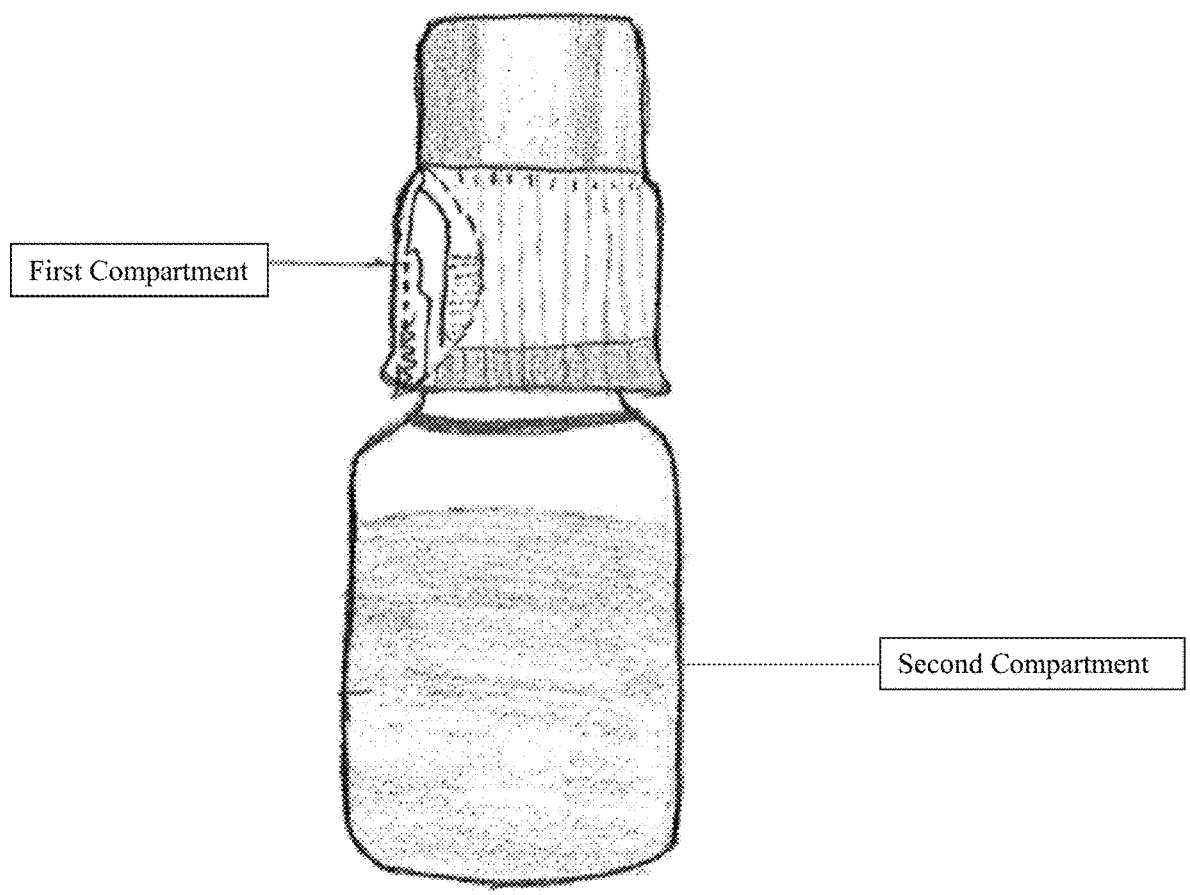
FIG. 1 shows a two-compartment vessel, which holds sodium picosulfate solution in a first compartment and a magnesium oxide and citric acid solution in a second compartment.

The above-described and other features will be appreciated and understood by those skilled in the art from the following detailed description, drawings, and appended claims.

DETAILED DESCRIPTION

The term "composition" as used herein refers to a dosage form suitable for oral administration, such as solution, powder, granules, spheroids, suspension, emulsion and the like, preferably solution.

The term "vessel" as used herein includes a bottle or other hollow container which can have multiple compartments as described herein.

The term "pharmaceutically acceptable" as used herein means that which is useful in preparing a pharmaceutical composition that is generally safe and non-toxic.

The term "excipients" as used herein means a component of a pharmaceutical product that is not an active ingredient such as, for example, basic agents, sweeteners, flavors, diluents, carriers and the like. The excipients that are useful in preparing pharmaceutical compositions and products that are generally safe and non-toxic.

One aspect relates to pharmaceutical products and liquid pharmaceutical compositions comprising sodium picosulfate, magnesium oxide and citric acid and process for their preparation.

Another aspect relates to a stable oral pharmaceutical product and liquid composition comprising sodium picosulfate, magnesium oxide and citric acid, wherein the sodium picosulfate is physically separated from a combination of magnesium oxide and citric acid.

Another aspect relates to a stable oral pharmaceutical preparation comprising sodium picosulfate in a first compartment and a combination of magnesium oxide and citric acid in a second compartment.

In another aspect, first compartment comprises sodium picosulfate and one or more pharmaceutically acceptable excipients in the form of liquid, and a second compartment comprises a combination of magnesium oxide and citric acid and one or more pharmaceutically acceptable excipients in the form of liquid.

Excipients may be selected from organic acids, mineral acids, alkalizing agents, preservatives, stabilizers, antioxidants, buffering agents, sweeteners, flavoring agents, and combinations thereof.

Exemplary organic acids include, but are not limited to tartaric acid, acetic acid, fumaric acid, succinic acid, lactic acid, citric acid, oxalic acid, malic acid, alone or in combination.

Exemplary mineral acids include, but are not limited to hydrochloric acid, phosphoric acid, sulfuric acid, alone or in combination.

Exemplary alkalizing agents include, but are not limited to sodium hydroxide, trisodium citrate dehydrate, potassium bicarbonate, sodium bicarbonate, potassium hydroxide, sodium carbonate, sodium phosphate, potassium phosphate, sodium acetate, sodium malate, alone or in combination.

Exemplary preservatives include, but are not limited to sodium benzoate, methyl paraben, propyl paraben, methyl paraben sodium, propyl paraben sodium, sorbic acid, benzyl alcohol, butyl paraben, ethyl paraben, benzalkonium chloride, benzoic acid, potassium benzoate, alone or in combination.

Exemplary stabilizers include, but are not limited to disodium edetate, xanthan gum and HP-βcyclodextrin, alginic acid, carrageenan, pectin, gellan gum, alone or in combination.

Exemplary antioxidants include, but are not limited to sodium metabisulfite, ascorbic acid, butyl hydroxy toluene, butyl hydroxy anisole, alone or in combination.

Exemplary buffering agents include, but are not limited to potassium hydrogen carbonate, citric acid monohydrate, trisodium citrate dehydrate, phosphoric acid, sodium phosphate, alone or in combination.

Exemplary sweeteners include, but are not limited to acesulfame potassium, sucralose, sodium saccharin, ammonium glycyrrhizinate, xylitol, sodium cyclamate, alone or in combination.

Exemplary flavoring agents include, but are not limited to, strawberry flavor, cranberry flavor, lemon flavor and orange flavor, alone or in combination.

As described in U.S. Pat. No. 9,827,231, citric acid and magnesium oxide may react with each other to become magnesium citrate and the unreacted magnesium oxide may accelerate the precipitation of magnesium citrate. If the pH of the preparation is kept low, the amount of precipitation tends to be reduced, but the sodium picosulfate becomes unstable. Hence, it is understood that, there were two different problems in the composition, i.e., precipitation of citric acid and magnesium oxide and stability problem of sodium picosulfate.

Accordingly, the present disclosure optionally involves use of at least one ingredient selected from organic acid, mineral acid and buffering agent to overcome the precipitation problem.

Figure 2:
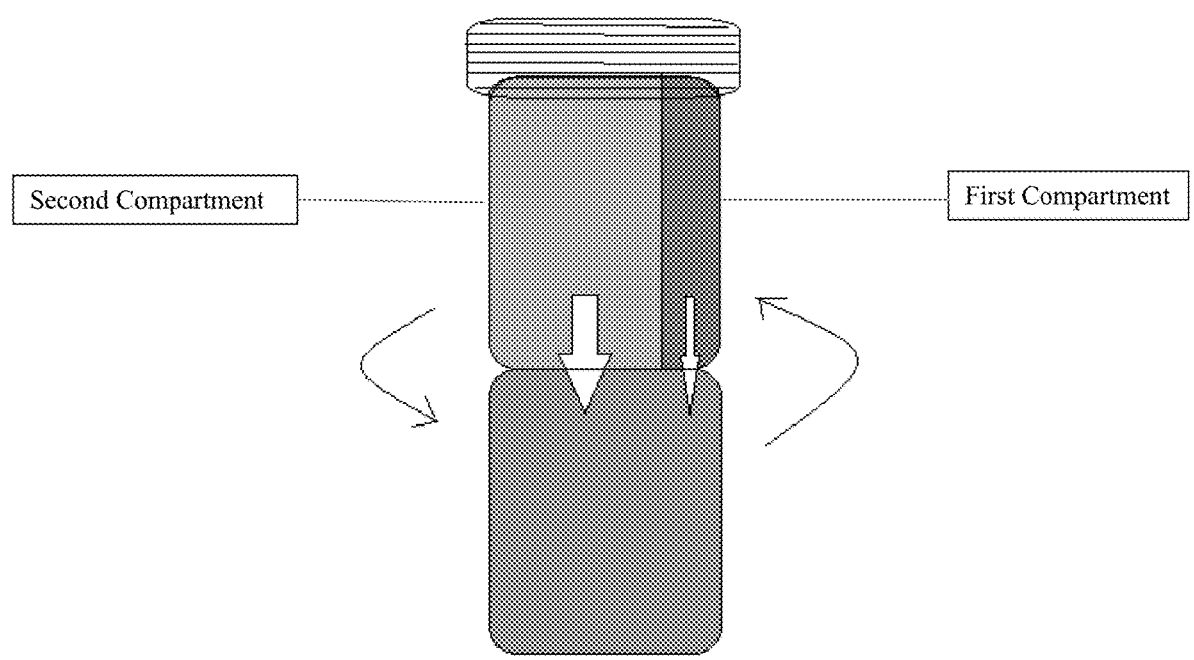
FIG. 2 shows a multi-compartment vessel, which holds sodium picosulfate solution in a first compartment and a magnesium oxide and citric acid solution in a second compartment.
Figure 3:
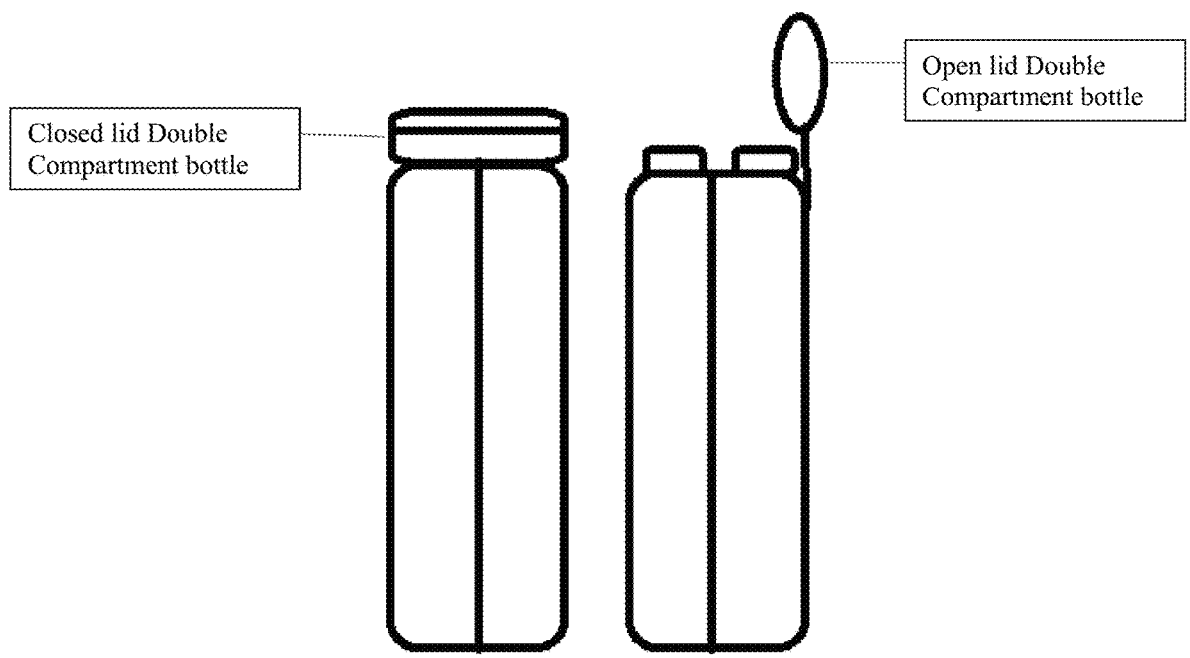
FIG. 3 shows a two-compartment vessel, which holds sodium picosulfate solution in a first compartment and a magnesium oxide and citric acid solution in a second compartment, wherein the vessel includes a lid separately sealing the first and second compartments.

To address the stability problem, sodium picosulfate was separated from the citric acid and magnesium oxide by using a two-compartment bottle (refer FIGS. 1, 2 and 3).

(4-[(Pyridin-2-yl) (4-hydroxyphenyl)methyl] phenyl sodium sulfate (RC-A) is one of the impurities in this pharmaceutical product, requiring special attention for its control.

The present disclosure provides a stable oral liquid composition and pharmaceutical product comprising (4-[(Pyridin-2-yl) (4-hydroxyphenyl)methyl] phenyl sodium sulfate impurity (RC-A) in an amount of less than 0.5% after storage for three months at 40° C.

The present disclosure provides a vessel comprising a hollow body that acts as a reservoir for pharmaceutical products. The vessel body can be divided into compartments to hold pharmaceutical products.

The vessel can be made of any material available in the art for storing and dispensing pharmaceutical products such that the material does not react with the pharmaceutical products stored within. Specifically, it can be made from glass, plastic, biocompatible polymers, other polymers and/or resins or combinations thereof. For example, as seen in FIG. 3, the lid can be made from a plastic material and the vessel body can be made from plastic.

The present disclosure provides a vessel comprising sodium picosulfate in a first compartment and a combination of magnesium oxide and citric acid in a second compartment, wherein the first and second compartment are physically separated from one another prior to dispensing, and wherein the vessel permits the components of the first and second compartments to be dispensed together.

The present disclosure provides a vessel comprising sodium picosulfate in a first compartment and a combination of magnesium oxide and citric acid in a second compartment, wherein the first and second compartments are designed such that the ingredients are initially separated from one another, but before administration they are mixed for simultaneous administration.

Exemplary ranges of components are provided in the following table expressed as % w/v.

| Component | Percentage/ Percentage range |
| --- | --- |
| Sodium picosulfate | 0.006 |
| Magnesium oxide | 7.500 |
| Citric acid | 2.188 |
| All excipients | 0.001-10 |
| Organic acids | 0.5-7.5 |
| Mineral acids | 2.5-10 |
| Alkalizing agents | 0.5-7.5 |
| Preservatives | 0.01-2 |
| Stabilizers | 0.01-2 |
| Antioxidants | 0.01-2 |
| Buffering agents | 0.01-10 |
| Sweeteners | 0.01-2 |
| Flavours | 0.01-1 |

In yet, another aspect the present disclosure relates to use of the present pharmaceutical products for cleansing of the colon as a preparation for colonoscopy in adults.

Certain specific aspects and embodiments of this invention are described in further detail by the examples below, which are provided only for purposes of illustration and are not intended to limit the scope of the invention in any manner.

EXAMPLES[4]

A=abbreviations used: Mg (milligrams), q.s. (quantity sufficient), RH (relative humidity), w/v (weight/volume)

Example 1

| Ingredient | Mg/bottle |
| --- | --- |
| I. First compartment | |
| Sodium picosulfate | 10.00 |
| Sodium benzoate | 5.00 |
| Purified water | q.s. |

| Ingredient | Mg/bottle |
|---|---|
| II. Second compartment | |
| Anhydrous citric acid | 12000.00 |
| Magnesium oxide | 3500.00 |
| Acesulfame potassium | 58.00 |
| Sodium benzoate | 85.00 |
| Sucralose | 200.00 |
| Disodium edetate | 210.00 |
| Tartaric acid | 4000.00 |
| Sodium metabisulfite | 320.00 |
| Strawberry flavor | 15.00 |
| Hydrochloric acid | q.s. |
| Purified water | q.s. |

Brief Manufacturing Process:
I. First Compartment
i. sodium benzoate was dissolved in purified water,
ii. sodium picosulfate was added to the solution of step (i) and the final volume was made up with purified water.
II. Second Compartment
i. anhydrous citric acid and magnesium oxide were dissolved in purified water,
ii. sodium benzoate, disodium edetate and sodium metabisulfite were added to the solution step (i),
iii. tartaric acid, sucralose, acesulfame potassium and strawberry flavors were added to the solution of step (ii),
iv. pH of the solution of step (iii), was adjusted using hydrochloric acid and the final volume was made up with purified water.

Stability Study:
Bottles were stored for three months at 40° C./75% RH, results are as follows:

| Impurities | Initial | 3 months at 40° C./75% RH |
|---|---|---|
| (4-[(Pyridin-2-yl) (4-hydroxyphenyl)methyl] phenyl sodium sulfate | 0.052 | 0.172 |
| Unknown impurities | 0.054 | 0.077 |
| Total Impurities | 0.106 | 0.249 |

Results of stability study reveals that, (4-[(Pyridin-2-yl) (4-hydroxyphenyl)methyl] phenyl sodium sulfate impurity and unknown impurities are within the acceptable limits. The limit of 4-[(Pyridin-2-yl) (4-hydroxyphenyl)methyl] phenyl sodium sulfate impurity is less than 0.5%.

Example 2

| Ingredient | Mg/bottle | % w/v |
|---|---|---|
| I. First compartment | | |
| Sodium picosulfate | 10.00 | 0.006 |
| Sodium benzoate | 10.00 | 0.006 |
| Disodium edetate | 210.00 | 0.131 |
| Sodium metabisulfite | 320.00 | 0.200 |
| Purified water | q.s. | — |
| II. Second compartment | | |
| Anhydrous citric acid | 12000.00 | 7.500 |
| Magnesium oxide | 3500.00 | 2.188 |
| Fumaric acid | 4000.00 | 2.500 |
| Tartaric acid | 4000.00 | 2.500 |
| Sodium hydroxide | 4200.00 | 2.625 |
| Sodium benzoate | 80.00 | 0.050 |
| Acesulfame potassium | 58.00 | 0.036 |
| Sucralose | 200.00 | 0.125 |
| Strawberry flavor | 15.00 | 0.009 |
| Purified water | q.s. | — |

Brief Manufacturing Process:
I. First Compartment
i. sodium benzoate, disodium edetate and sodium metabisulfite were dissolved in purified water,
ii. sodium picosulfate was added to the solution of step (i), and the final volume was made up with purified water.
II. Second Compartment
i. anhydrous citric acid and magnesium oxide were dissolved in purified water,
ii. fumaric acid and tartaric acid were added to the solution of step (i),
iii. the pH of the solution of step (ii), was adjusted between 4.5-5.0 using sodium hydroxide,
iv. sodium benzoate was dissolved in purified water,
v. acesulfame potassium, sucralose and strawberry flavor were added to the solution of step (iv),
vi. solution of step (v), was added to the solution of step (iii), and the final volume was made up with purified water.

Example 3

| Ingredient | Mg/bottle | % w/v |
|---|---|---|
| I. First compartment | | |
| Sodium picosulfate | 10.00 | 0.006 |
| Sodium benzoate | 10.00 | 0.006 |
| Disodium edetate | 210.00 | 0.131 |
| Purified water | q.s. | — |
| II. Second compartment | | |
| Anhydrous citric acid | 12000.00 | 7.500 |
| Magnesium oxide | 3500.00 | 2.188 |
| Hydrochloric acid | 35.00 | 0.022 |
| Acetic acid | 3752.00 | 2.345 |
| Sodium hydroxide | 4200.00 | 2.625 |
| Sodium benzoate | 80.00 | 0.050 |
| Acesulfame potassium | 58.00 | 0.036 |
| Sucralose | 200.00 | 0.125 |
| Strawberry flavor | 15.00 | 0.009 |
| Purified water | q.s. | — |

Brief Manufacturing Process:
I. First Compartment
i. sodium benzoate and disodium edetate were dissolved in purified water,
ii. sodium picosulfate was added to the solution of step (i), and the final volume was made up with purified water.
II. Second Compartment
i. anhydrous citric acid and magnesium oxide were dissolved in purified water,
ii. hydrochloric acid and acetic acid were added to the solution of step (i),
iii. the pH of the solution of step (ii) was adjusted between 4.5-5.0 using sodium hydroxide,
iv. sodium benzoate was dissolved in purified water, v. acesulfame potassium, sucralose and strawberry flavor were added to the solution of step (iv), vi. solution of step (v), was added to the solution of step (iii), and the final volume was made up with purified water.

Example 4

| Ingredient | Mg/bottle | % w/v |
|---|---|---|
| I. First compartment | | |
| Sodium picosulfate | 10.00 | 0.006 |
| Sodium benzoate | 10.00 | 0.006 |
| Purified water | q.s. | — |
| II. Second compartment | | |
| Anhydrous citric acid | 12000.00 | 7.500 |
| Magnesium oxide | 3500.00 | 2.188 |
| Potassium hydrogen carbonate | 500.00 | 0.313 |
| Sodium benzoate | 80.00 | 0.050 |
| Sodium saccharin | 66.00 | 0.041 |
| Strawberry flavor | 15.00 | 0.009 |
| Purified water | q.s. | — |

Brief Manufacturing Process:

I. First Compartment i. sodium benzoate was dissolved in purified water, ii. sodium picosulfate was added to the solution of step (i), and the final volume was made up with purified water.

II. Second Compartment i. anhydrous citric acid and magnesium oxide were dissolved in purified water, ii. potassium hydrogen carbonate and sodium benzoate were added to the solution step (i), iii. sodium saccharin and strawberry flavor were added to the solution of step (ii), and the final volume was made up with purified water.

Example 5

| Ingredient | Mg/bottle |
|---|---|
| I. First compartment | |
| Sodium picosulfate | 10.00 |
| Sodium benzoate | 5.00 |
| Purified water | q.s. |
| II. Second compartment | |
| Citric acid | 12000.00 |
| Magnesium oxide | 3500.00 |
| Acesulfame potassium | 58.00 |
| Sodium benzoate | 85.00 |
| Sucralose | 200.00 |
| Disodium edetate | 210.00 |
| Sodium metabisulfite | 320.00 |
| Strawberry flavor | 15.00 |
| Purified water | q.s. |

Brief Manufacturing Process:

I. First Compartment i. sodium benzoate was dissolved in purified water, ii. sodium picosulfate was added to the solution of step (i), and the final volume was made up with purified water.

II. Second Compartment i. citric acid and magnesium oxide were dissolved in purified water, ii. sodium benzoate, disodium edetate and sodium metabisulfite were added to the solution step (i), iii. sucralose, acesulfame potassium and strawberry flavors were added to the solution of step (ii), and the final volume was made up with purified water.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made, and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

We claim:

1. A stable oral liquid pharmaceutical product comprising: sodium picosulfate, and a combination of magnesium oxide and citric acid, wherein the sodium picosulfate is physically separated from the combination of magnesium oxide and citric acid in a two-compartment vessel, which holds a sodium picosulfate solution in a first compartment and a magnesium oxide and citric acid solution in a second compartment, wherein the vessel permits the components of the first and second compartments to be dispensed together simultaneously as a liquid solution, and wherein the first and second compartments do not include malic acid.

2. The pharmaceutical product of claim 1, comprising a (4-[(Pyridin-2-yl) (4-hydroxyphenyl)methyl] phenyl sodium sulfate impurity in an amount of less than 0.5% after storage for three months at 40° C.

3. The pharmaceutical product of claim 1, further comprising one or more pharmaceutically acceptable excipients selected from alkalizing agents, preservatives, stabilizers, antioxidants, buffering agents, sweeteners and flavoring agents.

4. A vessel comprising the first compartment and the second compartment of claim 1.

5. The vessel of claim 4, wherein the vessel further comprises a lid separately sealing the first and second compartments.

6. The vessel of claim 4, wherein the first and/or second compartment further comprises one or more pharmaceutically acceptable excipients selected from alkalizing agents, preservatives, stabilizers, antioxidants, buffering agents, sweeteners and flavoring agents.

7. A method of cleansing the colon of a subject as a preparation for colonoscopy, comprising administering the dispensed composition of claim 1.

\* \* \* \* \*